US012611492B2

(12) United States Patent
Indolfi et al.

(10) Patent No.: US 12,611,492 B2
(45) Date of Patent: Apr. 28, 2026

(54) LOCAL DRUG DELIVERY DEVICES AND METHODS FOR TREATING CANCER

(71) Applicants: Massachusetts Institute of Technology, Cambridge, MA (US); The General Hospital Corporation, Boston, MA (US)

(72) Inventors: Laura Indolfi, Boston, MA (US); Elazer R. Edelman, Brookline, MA (US); Robert S. Langer, Newton, MA (US); Jeffrey W. Clark, Chestnut Hill, MA (US); David T. Ting, Dover, MA (US); Cristina Rosa Annamaria Ferrone, Boston, MA (US); Matteo Ligorio, Boston, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 10 days.

(21) Appl. No.: 18/621,669

(22) Filed: Mar. 29, 2024

(65) Prior Publication Data

US 2024/0238485 A1     Jul. 18, 2024

Related U.S. Application Data

(60) Continuation of application No. 17/520,891, filed on Nov. 8, 2021, which is a division of application No. 15/055,012, filed on Feb. 26, 2016, now Pat. No. 11,167,066, which is a continuation of application No. 14/250,025, filed on Apr. 10, 2014, now Pat. No. 9,301,926.

(60) Provisional application No. 61/810,543, filed on Apr. 10, 2013.

(51) Int. Cl.
| | |
|---|---|
| *A61L 31/10* | (2006.01) |
| *A61F 2/04* | (2013.01) |
| *A61F 2/915* | (2013.01) |
| *A61K 9/00* | (2006.01) |
| *A61K 9/70* | (2006.01) |
| *A61K 31/337* | (2006.01) |
| *A61K 47/34* | (2017.01) |
| *A61L 31/14* | (2006.01) |
| *A61L 31/16* | (2006.01) |

(52) U.S. Cl.
CPC ............ *A61L 31/10* (2013.01); *A61K 9/0024* (2013.01); *A61K 9/0034* (2013.01); *A61K 9/7007* (2013.01); *A61K 31/337* (2013.01); *A61K 47/34* (2013.01); *A61L 31/148* (2013.01); *A61L 31/16* (2013.01); *A61F 2002/041* (2013.01); *A61F 2/915* (2013.01); *A61F 2230/0021* (2013.01); *A61L 2300/416*

(2013.01); *A61L 2300/604* (2013.01); *A61L 2300/606* (2013.01); *A61L 2420/06* (2013.01)

(58) Field of Classification Search
None
See application file for complete search history.

(56) References Cited

U.S. PATENT DOCUMENTS

| | | | |
|---|---|---|---|
| 5,716,981 | A | 2/1998 | Hunter et al. |
| 7,994,213 | B2 | 8/2011 | Shin et al. |
| 8,017,143 | B2 | 9/2011 | Shin et al. |
| 8,043,355 | B2 | 10/2011 | Shin et al. |
| 2005/0271701 | A1 | 12/2005 | Cottone et al. |
| 2008/0051882 | A1 | 2/2008 | Rubin |
| 2008/0167724 | A1 | 7/2008 | Ruane et al. |
| 2009/0099646 | A1 | 4/2009 | Matsuda et al. |
| 2010/0021519 | A1 | 1/2010 | Shenoy |
| 2011/0045055 | A1* | 2/2011 | Hingston .............. A61L 31/146 424/424 |
| 2011/0264190 | A1 | 10/2011 | McClain et al. |
| 2012/0128732 | A1 | 5/2012 | Trieu et al. |
| 2012/0150282 | A1 | 6/2012 | Adden et al. |
| 2012/0323311 | A1 | 12/2012 | McClain |
| 2013/0084322 | A1 | 4/2013 | Wu |

(Continued)

FOREIGN PATENT DOCUMENTS

| | | |
|---|---|---|
| EP | 2005980 A2 | 12/2008 |
| EP | 2238993 A2 | 10/2010 |

(Continued)

OTHER PUBLICATIONS

Jackon, J.K., et al., Characterization of perivascular poly(lactic-co-glycolic acid) films containing paclitaxel, International Journal of Pharmaceutics 283 (2004) 97-109 (Year: 2004).*

(Continued)

*Primary Examiner* — H. Sarah Park
(74) *Attorney, Agent, or Firm* — Eversheds Sutherland (US) LLP

(57) ABSTRACT

Drug-eluting devices and methods for the treatment of tumors of the pancreas, biliary system, gallbladder, liver, small bowel, or colon, are provided. Methods include deploying a drug-eluting device having a film which includes a mixture of a degradable polymer and a chemotherapeutic drug, wherein the film has a thickness from about 2 μm to about 1000 μm, into a tissue site and releasing a therapeutically effective amount of the chemotherapeutic drug from the film to treat the tumor, wherein the release of the therapeutically effective amount of the drug from the film is controlled by in vivo degradation of the polymer at the tissue site.

25 Claims, 9 Drawing Sheets

(56) References Cited

U.S. PATENT DOCUMENTS

| | | |
|---|---|---|
| 2013/0142875 A1 | 6/2013 | Shemi et al. |
| 2013/0236498 A1 | 9/2013 | Mangiardi |
| 2013/0280316 A1 | 10/2013 | Pal et al. |

FOREIGN PATENT DOCUMENTS

| | | |
|---|---|---|
| EP | 1997525 B1 | 2/2011 |
| JP | 2007-313009 A | 12/2007 |

OTHER PUBLICATIONS

Lu, L., et al., In vitro degradation of thin poly(DL-lactic-co-glycolicacid) films, J. Biomed. Mater. Res., 46: 236-244 (1999) (Year: 1999).*

Lu et al., "Effects of Amphiphilic PCL-PEG-PCL Copolymer Addition on 5-Fluorouracil Release from Biodegradable PCL Films for Stent Application," International Journal of Pharmaceutics, 2011, 419:77-84.

Ranganath, "The Use of Submicron/Nanoscale PLGA Implants to Deliver Paclitaxel with Enhanced Pharmacokinetics and Therapeutic Efficacy in Intracranial Glioblastoma in Mice," Biomaterials, 2010, 31:5199-5207.

Database WPI, week 201335; AN 2013-BC3395, CN 1027227944A, Oct. 17, 2012, XP00272811 (18 pages).

PCT International Search Report and Written Opinion for PCT Application No. PCT/US2014/033671 mailed Aug. 12, 2014 (12 pages).

Chung, M. J. et al., "Safety evaluation of self-expanding metallic biliary stents eluting gemcitabine in a porcine model," Journal of Gastroenterology and Hepatology 27 (2012) 261-267.

ClinicalTrials.gov, "Patency and Safety of the Drug Eluting Covered Biliary Stent Comparing to the Common Covered Biliary Stent (MIRA-cover)," (available at http://clinicaltrials.gov/ct2/show/study/NCT01512563) last updated Jan. 15, 2012.

Conroy, T. et al., " FOLFIRINOX versus Gemcitabine for Metastatic Pancreatic Cancer," The New England Journal of Medicine, 364:1817-25 (2011).

Guo, S.R. et al., "In vivo evaluation of 5-fluorouracil-containing self-expandable nitinol stent in rabbits: Efficiency in long-term local drug delivery," J Pharm Sci. Jul. 2010; 99(7):3009-18.

Hair, Clark D. et al., "Future developments in biliary stenting," Clinical and Experimental Gastroenterology 2013:691-99.

Han, Young-Min et al., "Polyurethane-Covered Self-Expandable Nitinol Stent for Malignant Biliary Obstruction: Preliminary Results," Cardiovasc Intervent Radiol (2002) 25:381-382.

Indolfi, Laura et al., Study—"Design of a Drug Eluting Stent for treatment of pancreatic malignancy," Abstract, Society for biomaterials (2013).

Lee et al., "The Effect on Porcine Bile Duct of a Metallic Stent Covered with a Paclitaxel-Incorporated Membrane," Gastrointest. Endosc. 61(2):296-301, Feb. 2005.

Ligorio, Matteo et al., "A novel drug-eluting platform for localized treatment of pancreatic cancer," Abstract, American Association for Cancer Research, Annual Meeting 2014, Apr. 5-9, 2014.

Si, Jang et al., "Porcine feasibility and safety of a new paclitaxel-eluting biliary stent with a Pluronic-containing membrane," Endoscopy 2012; 44:825-831.

Taewoong Medical, Taewoong Niti-STM biliary stents (available at http://www.stent.net/new/sub.php?localNum=2&pageNum=1&subNum=1&subNum2=2) accessedOct. 23, 2013.

Caves et al., "The Evolving Impact of Microfabrication and Nanotechnology on Stent Design," Journal of Vascular Surgery, 2006, pp. 1363-1368.

Jang et al., "Efficacy of a Metallic Stent Covered with a Paclitaxel-Incorporated Membrane Versus a Covered Metal Stent for Malignant Biliary Obstruction: A Prospective Comparative Study," Dig. Dis. Sci., 2013, 58:865-871.

Fredenberg et al. "The mechanisms of drug release in poly9lactic-co-glycolic acid)-based drug delivery systems—A review." Int'l J. Pharmaceutics, vol. 415, Issues 1-2, pp. 34-52 (Aug. 2011).

("flexible", Merriam_Webster Dictionary, available at https://www.merriam-webster.com/dictionary/flexible, accessed on Oct. 31, 2023.

* cited by examiner

100

102

102

106

104

LOCAL DRUG DELIVERY DEVICES AND METHODS FOR TREATING CANCER

CROSS-REFERENCE TO RELATED APPLICATION

This application is a continuation of U.S. application Ser. No. 17/520,891, filed Nov. 8, 2021, which is a divisional of U.S. application Ser. No. 15/055,012, filed Feb. 26, 2016, now U.S. Pat. No. 11,167,066, which is a continuation of U.S. application Ser. No. 14/250,025, filed Apr. 10, 2014, now U.S. Pat. No. 9,301,926, which claims priority to U.S. Provisional Patent Application No. 61/810,543, filed Apr. 10, 2013, which are each incorporated by reference herein.

TECHNICAL FIELD

The present disclosure is generally in the field of drug delivery devices and methods, and more particularly relates to implantable devices and methods providing controlled release of drug locally to tissue sites where needed, such as in treating tumors of the pancreas, biliary system, gallbladder, liver, small bowel, or colon.

BACKGROUND

Pancreatic cancer is the fourth most common cause of cancer-related death in the United States. (American Cancer Society Statistics, 2011). Ninety-four percent of patients diagnosed with pancreatic cancer die within 5 years of the diagnosis, giving pancreatic cancer the highest mortality rate of all major cancers. While a fifty-five percent increase in new pancreatic cancer cases is predicted over the next two decades, no early detection methods have been developed.

The most common form of pancreatic cancer is ductal adenocarcinoma (PDAC), which accounts for ninety-five percent of all pancreatic tumors. The vast majority of PDAC patients suffer from significant morbidity from local tumor growth, which include symptoms of abdominal pain, anorexia, nausea, vomiting, and jaundice. Unfortunately, the majority of diagnosed PDAC is not resectable, which limits therapies for local disease control to a combination of radiation and chemotherapy.

Despite the development of new anti-cancer agents, PDAC remains highly refractory to systemically delivered therapies, due in part to (i) impaired drug delivery caused by lack of local vasculature that limits drug distribution within the tumor and (ii) a fibrotic response to the tumor cells that restricts penetration of drug. These factors cannot be overcome by systemic therapies because of limited local residence and dose related toxicities that prevent use of high drug concentrations. For example, gemcitabine therapy has a ten percent response rate, and those regimens that increase response also increase systemic toxicity (e.g., FOL-FIRINOX regimen has a thirty-one percent response rate but with greater systemic toxicity). (Conroy, T. et al, New England J. Medicine, 364:1817-25 (2011)).

Accordingly, there remains a need for improved methods and devices for cancer therapy, in particular for reducing the problems associated with systemic administration of chemotherapeutic agents to treat tumors. It would be desirable to have better approaches for treating tumors in the pancreas and other intraperitoneal sites, the biliary system, gallbladder, liver, small bowel, and colon.

SUMMARY

In one aspect, methods are provided for treating a tumor of the pancreas, biliary system, gallbladder, liver, small bowel, or colon. The methods include (i) deploying a drug-eluting device into a tissue site of a patient in need of treatment, the device including a film which includes a mixture of a degradable polymer and a chemotherapeutic drug, wherein the film has a thickness from about 2 μm to about 1000 μm, and (ii) releasing a therapeutically effective amount of the chemotherapeutic drug from the film to the tissue site to treat the tumor, wherein the release of the therapeutically effective amount of the chemotherapeutic drug from the film is controlled by in vivo degradation of the polymer at the tissue site.

In another aspect, drug-eluting devices are provided for the treatment of a tumor of the pancreas, biliary system, gallbladder, liver, small bowel, or colon. The devices include a film having a thickness from about 2 μm to about 1000 μm and including a mixture of a degradable polymer and a chemotherapeutic drug, wherein the device is configured for deployment into a tissue site of a patient, the film being configured to provide controlled release, by in vivo degradation of the polymer at the tissue site, of a therapeutically effective amount of the chemotherapeutic drug to the tissue site to treat the tumor.

DETAILED DESCRIPTION

Figure 1A:
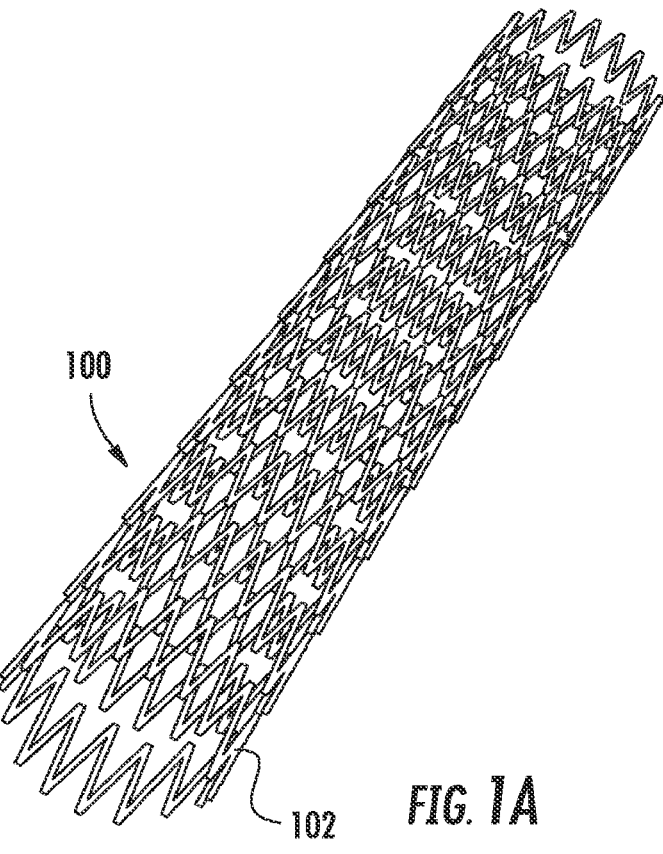
FIG. 1A is a perspective view of one embodiment of a drug-eluting device in the form of a stent.

Improved local drug delivery systems have been developed which are capable of effectively delivering chemotherapeutic agents to tumors in higher doses compared to IV systemic administration. The systems surprisingly were found to be capable of achieving five times the drug presence and distribution within the tumor as compared to IV therapy in an animal model. Accordingly, these devices and methods advantageously bypass known therapeutic obstacles and may provide local delivery of high levels of a conventional, as well as novel, cytotoxic agents for effective tumor cell cytotoxicity and minimal bystander cell toxicity.

The methods and devices utilize a mixture of a degradable polymer and a chemotherapeutic drug, wherein the mixture is in the form of a film having a thickness from about 2 μm to about 1000 μm and wherein the film is configured to provide controlled release, by in vivo degradation of the polymer at the tissue site, of a therapeutically effective amount of the chemotherapeutic drug to the tissue site of the tumor. For instance, the methods and devices may be used to locally treat tumors of the pancreas, biliary system, gallbladder, liver, small bowel, or colon, among others. In certain embodiments, the device is deployed into a pancreatobiliary or intraperitoneal tissue site. For example, these devices may be placed in the pancreatobiliary tree to direct the drug to its target and prevent closure of the pancreatobiliary tract by cancer cell growth. As such, these methods and devices may also be suitable for treatment of other cancers of the biliary tree including but not limited to cholangiocarcinoma, gallbladder cancer, lymphoma, and metastatic tumors.

Drug-Eluting Devices

In certain embodiments, as shown in FIGS. 1-3, a drug-eluting device for the treatment of a tumor of the pancreas, biliary system, gallbladder, liver, small bowel, or colon, is provided. The device includes a film having a thickness from about 2 μm to about 1000 μm and including a mixture of a degradable polymer and a chemotherapeutic drug. The device is configured for deployment into a tissue site of a patient, the film being configured to provide controlled release, by in vivo degradation of the polymer at the tissue site, of a therapeutically effective amount of the chemotherapeutic drug to the tissue site to treat the tumor. For example, the tissue site may be a biliary or pancreatic duct.

As used herein, the term "film" refers to a relatively thin coating, layer, patch, or sheet-like structure formed at least in part of the mixture of the degradable polymer and the chemotherapeutic drug. As is described in more detail throughout this disclosure, the film may be self-supporting or may be adhered or otherwise disposed on a supporting substratum. The film may be flexible or rigid. In certain embodiments, the film has a thickness from about 5 μm to about 500 μm. In one embodiment, the film has a thickness of less than about 100 μm. In one embodiment, the film has a thickness from about 5 μm to about 100 μm. However, it should be understood that the film thickness ranges disclosed herein are merely exemplary, and that other film thicknesses, including thicknesses above about 1000 μm, may be used without departing from the spirit of the present disclosure.

The film includes a mixture of a degradable polymer and a chemotherapeutic drug and is configured to provide controlled release of the drug by in vivo degradation of the polymer at the tissue site. In one embodiment, the mixture includes from about 1 weight percent to about 10 weight percent of the chemotherapeutic drug. In one embodiment, the film is configured to release drug in an amount of about 0.5 pg to about 1000 mg per week.

For example, the polymer may be any suitable biodegradable polymer known in the art. Examples of suitable polymeric materials include synthetic polymers selected from poly(amides), poly(esters), poly(anhydrides), poly(orthoesters), polyphosphazenes, pseudo poly(amino acids), poly (glycerol-sebacate), copolymers thereof, and mixtures thereof. For example, a suitable polymer may be formed from poly(lactic acids), poly(glycolic acids), poly(lactic-co-glycolic acids), poly(caprolactones), and mixtures thereof.

In a preferred embodiment, the degradable polymer is poly(lactic-co-glycolic acid) (PLGA). For example, the film may contain PLGA copolymers with or without ester terminations, including but not limited to PLGA 50:50, 75:25, and 65:35. Advantageously, PLGA and other degradable polymers may provide the ability to modulate the drug release kinetics of the film, as compared to certain other polymeric materials, such as polyurethane, with which controlling release kinetics is more difficult.

In one embodiment, the degradable polymer is a hydrolytically degradable polymer. That is, the polymer undergoes hydrolytic bond cleavage resulting in polymer degradation. For example, release of the drug from the film may be controlled by non-enzymatic, hydrolytic degradation of the polymer at the tissue site. Such a drug release kinetics profile may be particularly desirable for implantation sites, such as pancreatobiliary sites, where the presence of enzymes is high. Indeed, the pancreas is one of the most challenging organs for designing and manufacturing a dedicated drug-eluting platform because of its anatomical position along with its massive production of digestive enzymes.

Prior attempts were made to design a pancreatobiliary drug-eluting stent using a polyurethane based method to treat PDACs. (see Lee et al., "The Effect on Porcine Bile Duct of a Metallic Stent Covered with a Paclitaxel-Incorporated Membrane," *Gastrointest. Endosc.* 61(2): 296-301, February 2005). However, these devices were limited in their ability to control polymer erosion and thus maintain adequate sustained drug release. Specifically, erosion of the polyurethane allowed the formation of superficial cracks in the polymer, thus causing unpredictable drug release. Because a reliable and predictable in vivo polymer degradation/drug release profile is important, that earlier work failed to show improvements in the clinical outcome. Accordingly, it is desirable that hydrolytic bulk degradation of the polymer occurs via the surrounding fluids imbibing the coating layer, to trigger bulk degradation and initiate drug release, without causing superficial cracks. As described in more detail herein, such controllable hydrolytic bulk degradation without cracking has been observed with PLGA.

In one embodiment, the degradable polymer includes a radiation-sensitive polymer configured to release the drug in response to the patient being exposed to radiation.

As is discussed in further detail in the Examples section, the film may be prepared by solvent evaporation in a solution having a concentration of about 5 to about 40 percent weight by volume of the polymer. In certain embodiments, the film is prepared by solvent evaporation in a solution having a concentration of about 10 to about 30 percent weight by volume of the polymer.

The film optionally may include one or more pharmaceutically acceptable excipients. For example, the one or more pharmaceutically acceptable excipients may be combined in the mixture with the degradable polymer and the chemotherapeutic agent.

The chemotherapeutic drug may be any drug formulation effective to treat cancer by inhibiting the growth and/or invasiveness of malignant cells and/or inducing cytotoxicity by apoptosis or necrosis of malignant cells. The chemotherapeutic agent may be a taxane or platinum drug known for use in treating cancer. In certain embodiments, the chemotherapeutic drug is selected from the group consisting of paclitaxel, gemcitabine, nab-paclitaxel, 5-fluorouracil, oxaliplatin, irinotecan, and combinations thereof. In certain embodiments, the chemotherapeutic drug includes an MEK inhibitor, a PI3K inhibitor, a Hedgehog inhibitor, a Wnt inhibitor, or a combination thereof. In certain embodiments, the drug includes an agent that interferes with the mTOR or NfKb pathways. In certain embodiments, the chemotherapeutic drug is a drug, such as a novel therapeutic, that displays poor systemic delivery or dose limited toxicities. For example, the chemotherapeutic drug may be a phase I drug that was promising in preclinical trials, but was found to be poorly or not tolerable with systemic dosing. The chemotherapeutic drug may be selected from new classes of therapies, such as siRNA-Alnylam type therapies, where delivery has traditionally been rate-limiting.

In a preferred embodiment, the chemotherapeutic drug is paclitaxel and the degradable polymer is poly(lactic-co-glycolic acid). For example, for such a film composition, the therapeutically effective amount may be at least about 1 mg/day of the paclitaxel. In one embodiment, the therapeutically effective amount may be a mean average amount of from 5 mg/day to 125 mg/day of the paclitaxel.

In certain embodiments, bulk degradation of the film is tunable from a few days to several months (e.g., 12 months or more). In one embodiment, the film is configured to degrade within a period of about 1 day to about 12 months after deployment, for example between 30 and 120 days. In one embodiment, the film is configured to degrade within a period of less than 2 years.

In certain embodiments, the device is configured to release the chemotherapeutic drug according to a defined release kinetics profile. For example, the release kinetics profile may include a delay period from about 1 day to about 14 days after deploying of the device into the tissue site. For example, during the delay period a sub-therapeutically effective amount of the drug may be released (e.g., by diffusion of drug present on or at the surface of the film). The delay advantageously facilitates at least some healing of normal tissues at the deployment site (e.g., adjacent to the tumor) before release of exposure to (the relatively larger) therapeutically effective of amounts of the chemotherapeutic agent. This release profile reduces the risk of infection, perforation, bleeding, and other complications. That is, the delay period avoids a burst release and allows enough time for the patient to recover from surgery before the chemotherapeutic drug is released.

After the delay, or slow release, period, acceleration of release to a therapeutically effective level occurs. For example, the film may be configured to provide an initial release rate of the chemotherapeutic drug which is substantially linear, following the delay period. In one embodiment, the release of the therapeutically effective amount of the chemotherapeutic drug, after the delay period, has an initial release rate that is substantially linear for at least 3 days.

In certain embodiments, the therapeutically effective amount of the drug is released over a treatment period of about 10 days to about 1 year. In one embodiment, a therapeutically effective amount of drug is released over a treatment period from about 10 days to about 90 days. In one embodiment, a therapeutically effective amount of drug is released over a treatment period of about 30 days. In certain embodiments, an initial release of drug at a substantially linear release starts from about day 5 up to about 60 days. Thus, a high concentration of the drug is locally released over a short period of time. This aggressive treatment regime attacks the tumor and makes it regress in the shortest time possible.

The release kinetics profile of the film may be tailored based on the selection of the degradable polymer. For example, PLGA displays a biphasic release profile, as diffusion and degradation provide two different release peaks. Accordingly, PLGA displays a highly tunable sustained release profile including an initial lag or delay, an initial linear release period, then a release plateau.

These devices can be fabricated in various shapes and sizes to adapt to different deployment sites and methods. For example, the tissue site may be a pancreatobiliary tissue site, in which case a stent or tubular device may be preferred, or the tissue site may be an intraperitoneal tissue site, in which case a mesh or patch-type device may be preferred. The device may be implanted in an open surgical procedure or laparoscopically.

In certain embodiments, the device further includes a biocompatible substratum to which the film is adhered or otherwise fixed. For example, the substratum may be any suitable structure for implantation in a patient at a desired tissue site. For example, the substratum may be a stent, tube, patch, or mesh structure. The substratum may be flexible or rigid. The substratum may be made of any suitable material or combination of materials. For example, the substratum may include a metal, a polymer, or a ceramic material. In certain embodiments, the substratum includes stainless steel alloy, cobalt chromium alloy, nitinol, platinum alloy, titanium alloy, silicone, expanded polytetrafluoroethylene (ePTFE), or polyethylene.

Figure 1B:
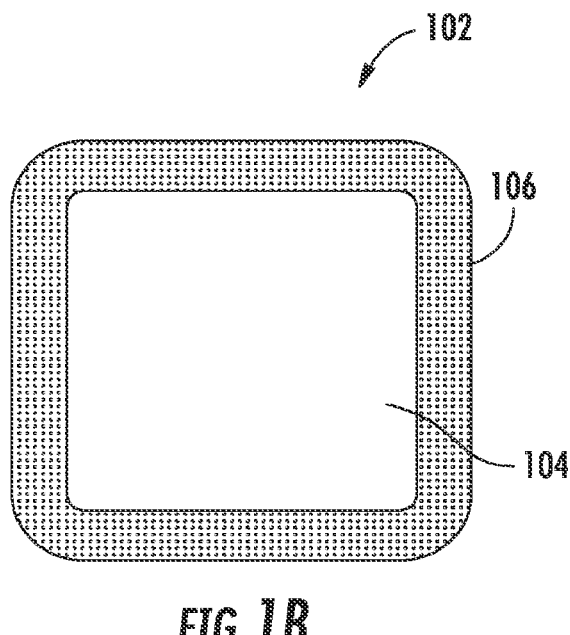
FIG. 1B is a cross-sectional view of one of the struts of the stent of FIG. 1A.

In certain embodiments, the device may be configured to be inserted into a biliary or pancreatic duct of a patient. The term "configured" in this embodiment means that the device has suitable dimensions, geometry, materials of construction, flexibility/softness (e.g., durometer value) for insertion and use within a biliary or pancreatic duct of a patient. For example, the device may be configured to prevent closure of a pancreatic duct in which it is deployed. For example, a drug-eluting stent may reduce stent re-occlusion, which is a common complication for pancreatic and biliary cancer patients who receive stents for biliary obstructions. One embodiment is shown in FIGS. 1A-1B. Drug-eluting stent 100 includes struts 102 having a film 106 disposed on strut substratum 104.

In various embodiments, the stent may be a balloon expanding or self-expandable stent, or the stent may be non-expanding. The stent may or may not have open lattice structure. That is, the stent may or may not have one or more apertures in the sidewall. The stent also may or may not have anchoring flaps at their ends. In one embodiment, the stent has a length of about 0.5 cm to about 18 cm and a diameter of about 2 mm to about 30 mm. For example, a stent may have a length of about 3 cm to about 18 cm and a diameter of about 2 mm to about 10 mm.

Figure 3A:
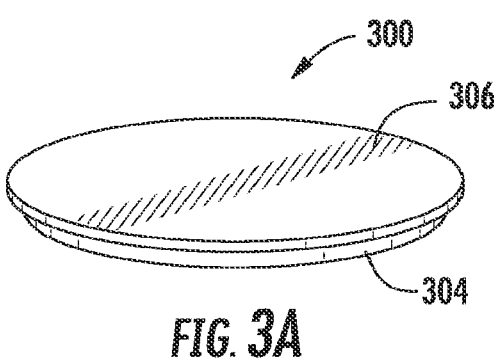
FIG. 3A is a perspective view of one embodiment of a drug-eluting device.
Figure 3B:
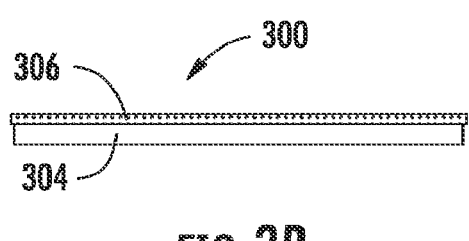
FIG. 3B is a cross-sectional view of the drug-eluting device of FIG. 3A.

As shown in FIGS. 3A-3B, device 300 includes a substratum patch 304 having a film 306 disposed thereon. The patch may be rigid or flexible. The substratum may also be a flexible or rigid mesh on which the film is disposed. In certain embodiments, the device is configured to be implanted directly onto the tumor.

Figure 2A:
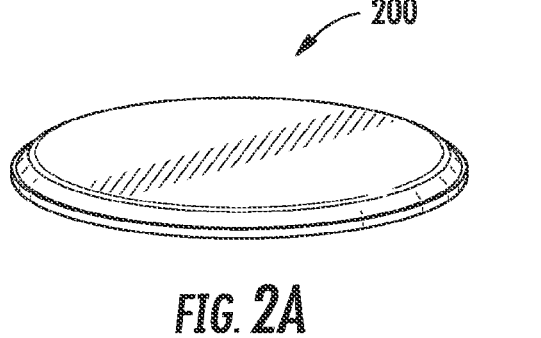
FIG. 2A is a perspective view of one embodiment of a drug-eluting device.
Figure 2B:
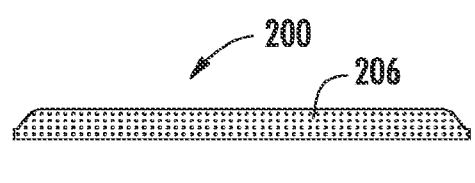
FIG. 2B is a cross-sectional view of the drug-eluting device of FIG. 2A.

In certain embodiments, as shown in FIGS. 2A-2B, the device 200 includes film 206, which is self-supporting, and is not supported by a substratum. The device may be a flexible/foldable or rigid patch-type device. In certain embodiments, the device is configured to be implanted directly onto the tumor. Other substratum constructions and geometries are also envisioned.

In certain embodiments, the film may be adhered to or disposed on the substratum by spray coating, dip coating, sintering, or any form of adhesion or coating on any aspect or part of the substratum. Other coating techniques may be used and are known to those of ordinary skill in the art. In certain embodiments, the film is adhered to the substratum in a uniform thickness of about 2 to about 500 μm. For example, the film may have a uniform thickness of about 10 to about 100 μm. In certain embodiments, the film is a homogenous, smooth, nonporous composition having a uniform thickness. The thickness may be selected based on the desired degradation/release kinetics and the total drug payload needed, for example.

In other embodiments, the coating may be deposited in an array of discrete regions in or on the substratum. In one example, the substratum may have a plurality of through-holes or concave regions which serve as reservoirs and are loaded with the drug coating material.

Methods of Treatment

In certain embodiments, methods of treating a tumor of the pancreas, biliary system, gallbladder, liver, small bowel, or colon, are provided, including: (i) deploying a drug-eluting device into a tissue site of a patient in need of treatment, the device having a film which includes a mixture of a degradable polymer and a chemotherapeutic drug, wherein the film has a thickness from about 2 μm to about 1000 μm, and (ii) releasing a therapeutically effective amount of the chemotherapeutic drug from the film to the tissue site to treat the tumor, wherein the release of the therapeutically effective amount of the chemotherapeutic drug from the film is controlled by in vivo degradation of the polymer at the tissue site. The drug-eluting device may include any of the device, film, polymer, drug, substratum, or other features described herein, as well as alternatives thereof, which are also meant to fall within the scope of this disclosure.

In one embodiment, release of the therapeutically effective amount of the chemotherapeutic drug has a substantially linear rate of release following a delay period of from about 1 day to about 14 days after deploying of the device into the tissue site. For example, the delay period may be from about 2 to about 4 days. In certain embodiments, a sub-therapeutically effective amount of the drug is released during the delay period.

In one embodiment, the chemotherapeutic drug is paclitaxel and the degradable polymer is poly(lactic-co-glycolic acid). For example, for such a film composition, the therapeutically effective amount may be at least about 1 mg/day of the paclitaxel. In one embodiment, the therapeutically effective amount may be a mean average amount of from 5 mg/day to 125 mg/day of the paclitaxel. In one embodiment, a therapeutically effective amount of drug is released over a treatment period from about 10 days to about 90 days. In one embodiment, the degradable polymer is configured to degrade within a period from about 1 day to about 12 months after deployment.

In embodiments in which the device includes a substratum, deploying the device may include inserting the device into a biliary or pancreatic duct of the patient or implanting the device directly onto the tumor. In one embodiment, the substratum is a balloon-expanding stent and the step of deploying the device includes inflating a balloon to expand the stent.

The drug-eluting devices and methods described herein may be used together with current systemic chemotherapy, external radiation, and/or surgery to prolong survival in patients. These devices and methods advantageously provide local delivery of chemotherapy for treatment of pancreatobiliary cancers. It is believed that modification of known drug delivery barriers (i.e., hypovascularity and significant desmoplastic stromal response) can sensitize pancreatic primary tumor cells to standard doses of cytotoxic therapies. Therefore, these devices and methods may utilize conventional cytotoxics with efficacy in pancreatic cancer, as well as novel treatment agents that cannot be tolerated in systemic administration.

The drug-eluting devices and methods described herein may be more fully understood in view of the following examples.

EXAMPLES

Using in vitro and in vivo animal studies, it was determined that a film-based device configured to release chemotherapeutic agents can be used to locally treat adenocarcinomas.

In Vitro Studies

Figure 4:
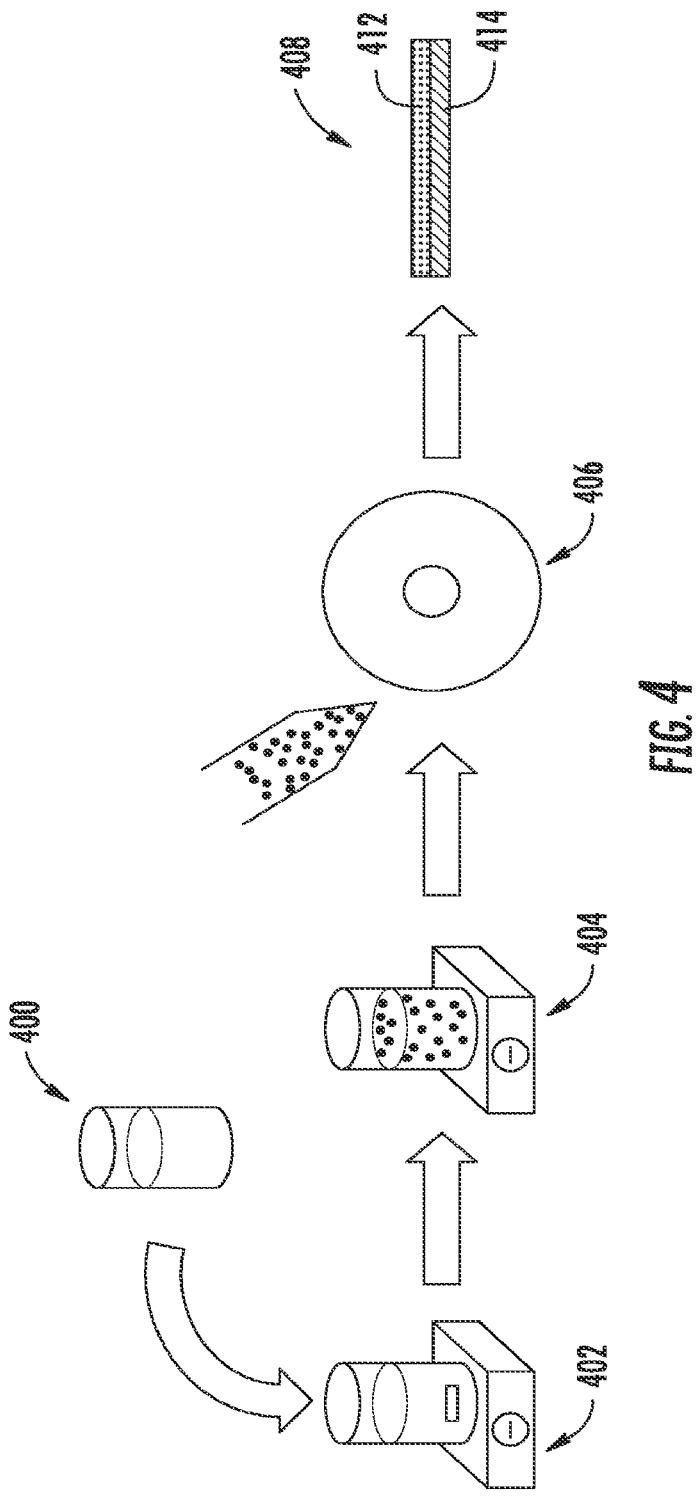
FIG. 4 is a process diagram illustrating one embodiment of a method for making drug-eluting devices.

Drug-polymer film coated substratum samples were prepared according to the process shown in FIG. 4. Specifically, a solution of paclitaxel in acetone 400 was combined with a solution of PLGA in acetone 402 to form a solution of paclitaxel and PLGA in acetone 404. This solution was poured onto a stainless steel disc 406 and then the solvent was evaporated to form sample 408 having a drug-polymer film 412 coated on the substratum 414.

Figure 8:
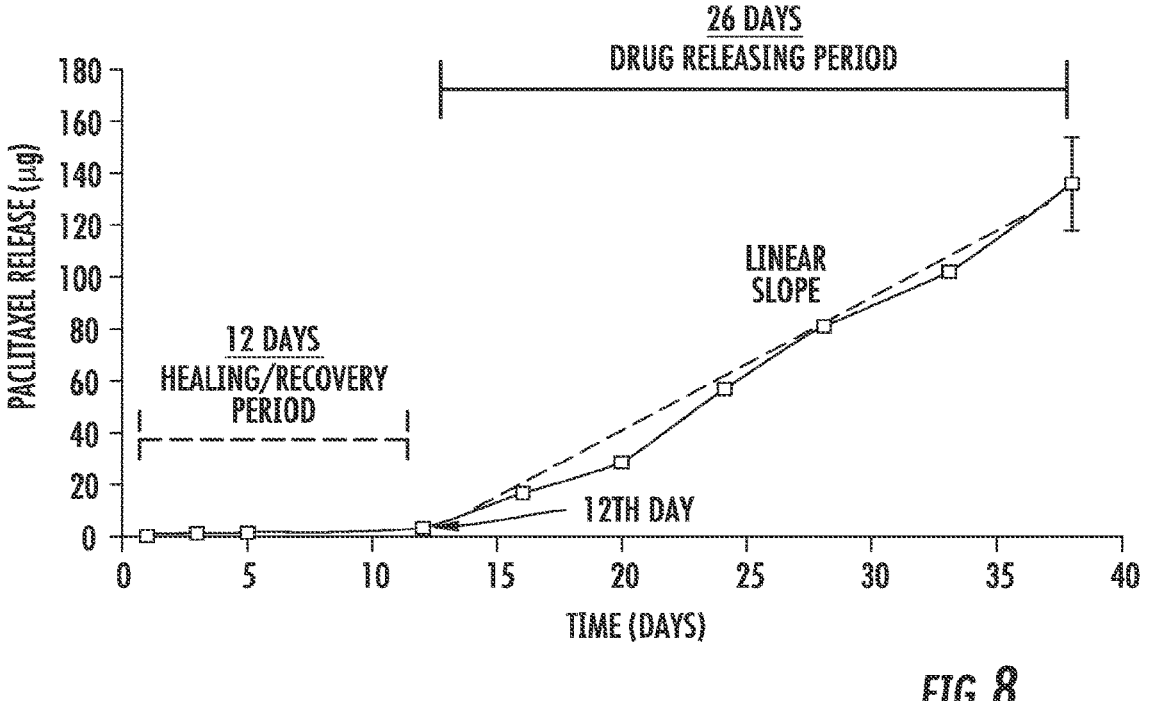
FIG. 8 is a graph showing the amount of paclitaxel released over time from a drug-eluting device in vitro.

In one example, PLGA 50:50 (Resomer® RG502) was dissolved in acetone at several concentrations: 5%, 10%, and 20% w/v, and combined with solutions containing 200 μg paclitaxel (Invitrogen®). Each PLGA-paclitaxel solution was stirred and poured onto an AISI 316L stainless steel 6 mm disc. To study the drug release of the devices, a ratio 1:250 of fluorescent drug was added to the solution, and the disc was put in PBS and incubated at 37° C. At selected times, an aliquot of supernatant was analyzed and replaced by fresh media. FIG. 8 shows the amount of paclitaxel released from the sample made with 10% w/v PLGA. This sample showed a delayed onset of the release kinetics and a sustained ongoing release after ten days.

Figure 9:
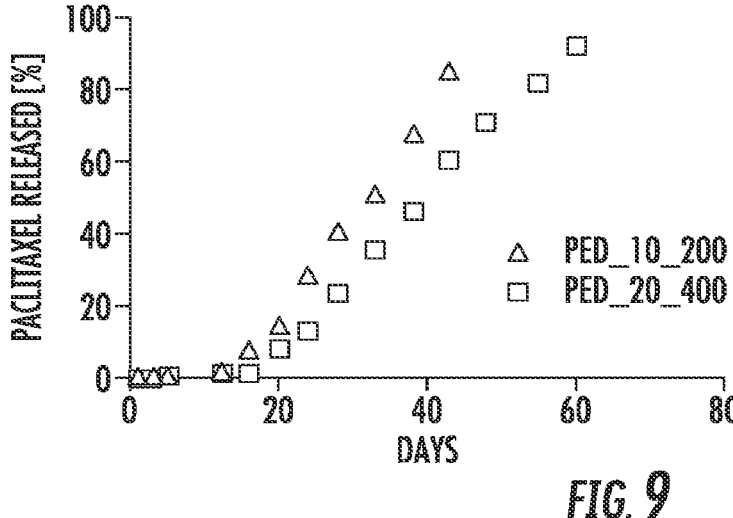
FIG. 9 is a graph showing the percentage of paclitaxel released over time from drug-eluting devices with varying film compositions in vitro.
Figure 10:
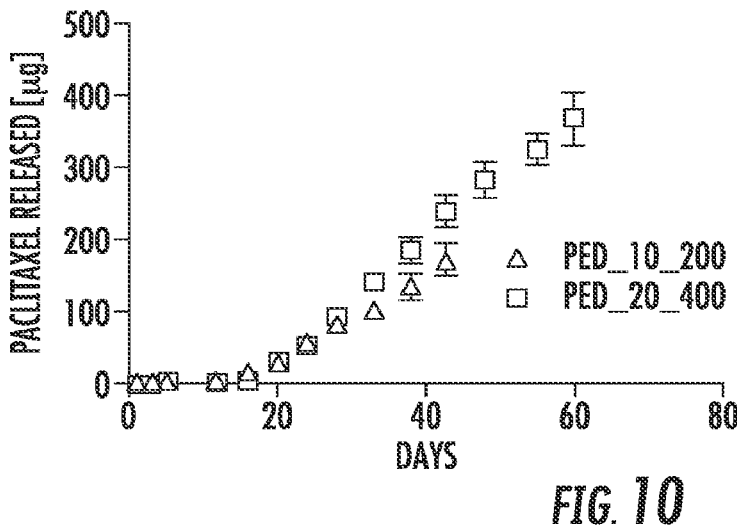
FIG. 10 is a graph showing the amount of paclitaxel released over time from drug-eluting devices with varying film compositions in vitro.

In another example, two different samples were tested: stainless steel discs coated with PED_10_200 and PED_20_400, differing one from the other in PLGA concentration (10 or 20% w/v) and paclitaxel amount (200 or 400 μg). FIGS. 9 and 10 show the percent and amount of paclitaxel released over time. It was observed that the concentration of the polymer in the film could be used to tune the release profile of the drug.

The samples were also fully characterized in terms of weight, morphology, and thickness of the film coating. Surface chemical characterization was carried out by analysis in dispersion of energy (EDAX, Oxford mod. INCA 200) using scanning electron microcopy (SEM, Leica 420). The electron microscopy analysis showed a homogeneous, smooth, non-porous PLGA layer coating the metallic surface. Morphological depictions showed a uniform surface appearance, with no cracks or bubbles observed, and homogeneous distribution of paclitaxel. Analyses were also performed at different locations along the coating surface where each measurement confirmed the presence of polymeric atomic elements at the expected stoichiometric ratio.

Figure 5:
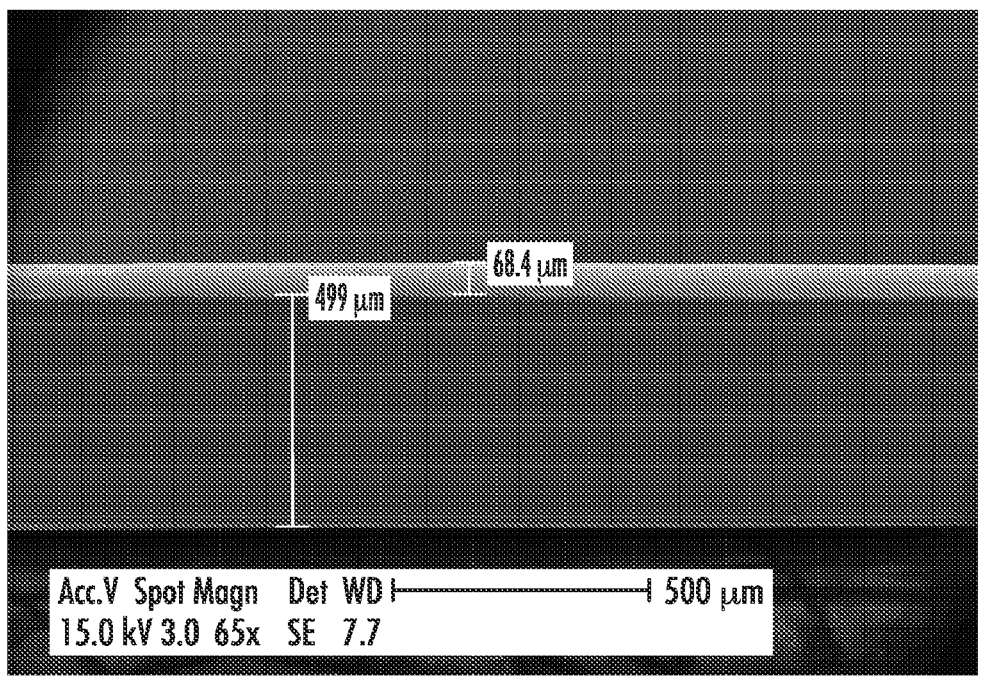
FIG. 5 is a scanning electron microscopic photograph of a drug-eluting device.
Figure 6:
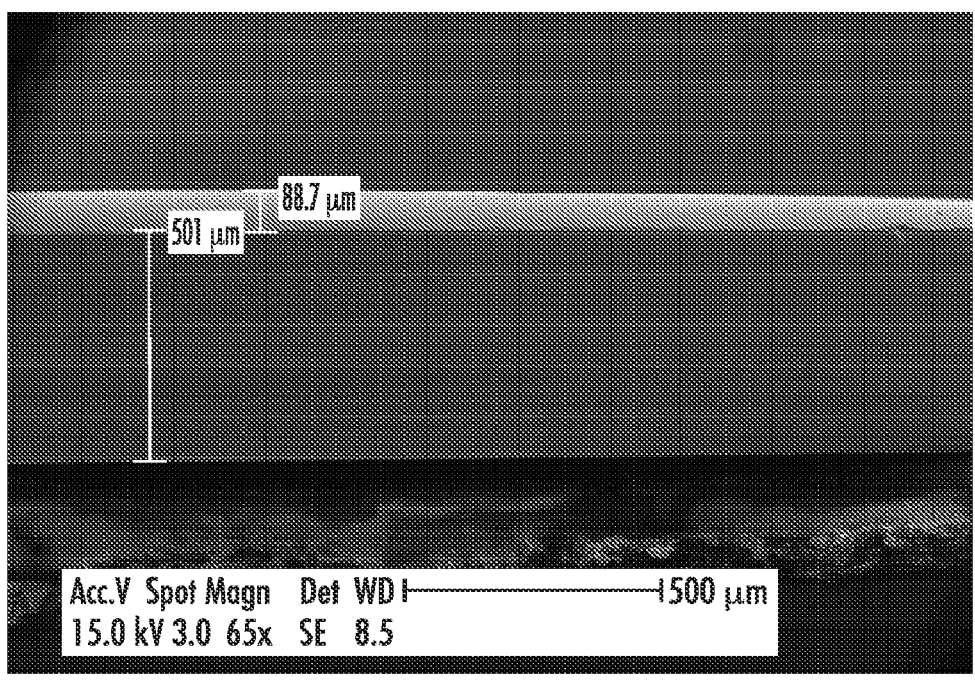
FIG. 6 is a scanning electron microscopic photograph of a drug-eluting device.

As illustrated in FIGS. 5-6, thickness was calculated using the SEM software revealing a constant value in all the investigated locations. FIG. 5 depicts the thickness (~70 μm), uniformity, and homogeneity of the PED_10_200 film on a 316L stainless steel disc having a thickness of approximately 500 μm. FIG. 6 depicts the thickness (~90 μm), uniformity, and homogeneity of the PED_20_400 film on a 316L stainless steel disc having a thickness of approximately 500 μm. It was found that the thickness of the coating layer may be modulated through an opportune selection of the polymer concentration. This observation is critical given the tight relationship of PLGA degradation kinetics, and therefore the elution rate of paclitaxel, as a function of thickness. Specifically, this methodology resulted in a platform technology ensuring similar outcomes for different formulations, as highlighted by the small difference in thickness between PED_10_200 and PED_20_400 (see FIGS. 5-6, 9-10).

In summary, controlled release of fluorescently-labeled paclitaxel lasting for more than one month was achieved from samples where the release kinetics were highly tunable using different ratios of PLGA and paclitaxel. In particular, a delayed release buffer period could be modulated with increasing polymer concentration in the organic phase. This initial formulation-dependent delay could be tailored to allow adequate healing time for patients following surgical implantation. After this healing phase, the device would release its drug payload at a steady and predictable rate, including an initially linear release period. Moreover, the device can be designed to release different amounts of chemotherapeutic agent with similar kinetics. By doubling both the drug content and polymer concentration, the film formulations were tuned to accomplish an initial linear release of paclitaxel (see FIGS. 8-10). Additionally, the dose released increase and the in vitro time of treatment increased from 45 days (for the lower dose) to 60 days (for the higher dose) (see FIGS. 8-10).

For implanted devices, biocompatibility and sterility is a foremost requirement. Therefore, the interaction between UV sterilized devices and Endothelial Cell culture overtime was also tested. The coated discs were sterilized overnight under UV. Cells in contact with the sterilized coated disc were observed to be vital and displayed normal growth and morphology. No bacterial or fungal contamination was found after 3 days of co-culture. Moreover, incubation of the samples in aqueous media verified great adherence to the metallic substratum as shown by the presence of coating at later time points and homogenous polymer degradation.

The in vitro studies show the ability to achieve a polymeric film coating on a substratum and to optimize the interface properties, adhesion, degradation, and drug release kinetics. By changing processing conditions (e.g., polymer: solvent ratio, amount of drug, evaporation time, evaporation condition), it is possible to modulate thickness of the coating layer, and thereby tailor the degradation kinetics of the film. For example, because the release profile is a function of polymer thickness, the kinetic profiles of these devices may be easily tailored, such that a device's pharmaceutical activity can be selected by simply adjusting coating parameters to match the need of the patient.

In Vivo Studies

Figures 11, 12, 13:
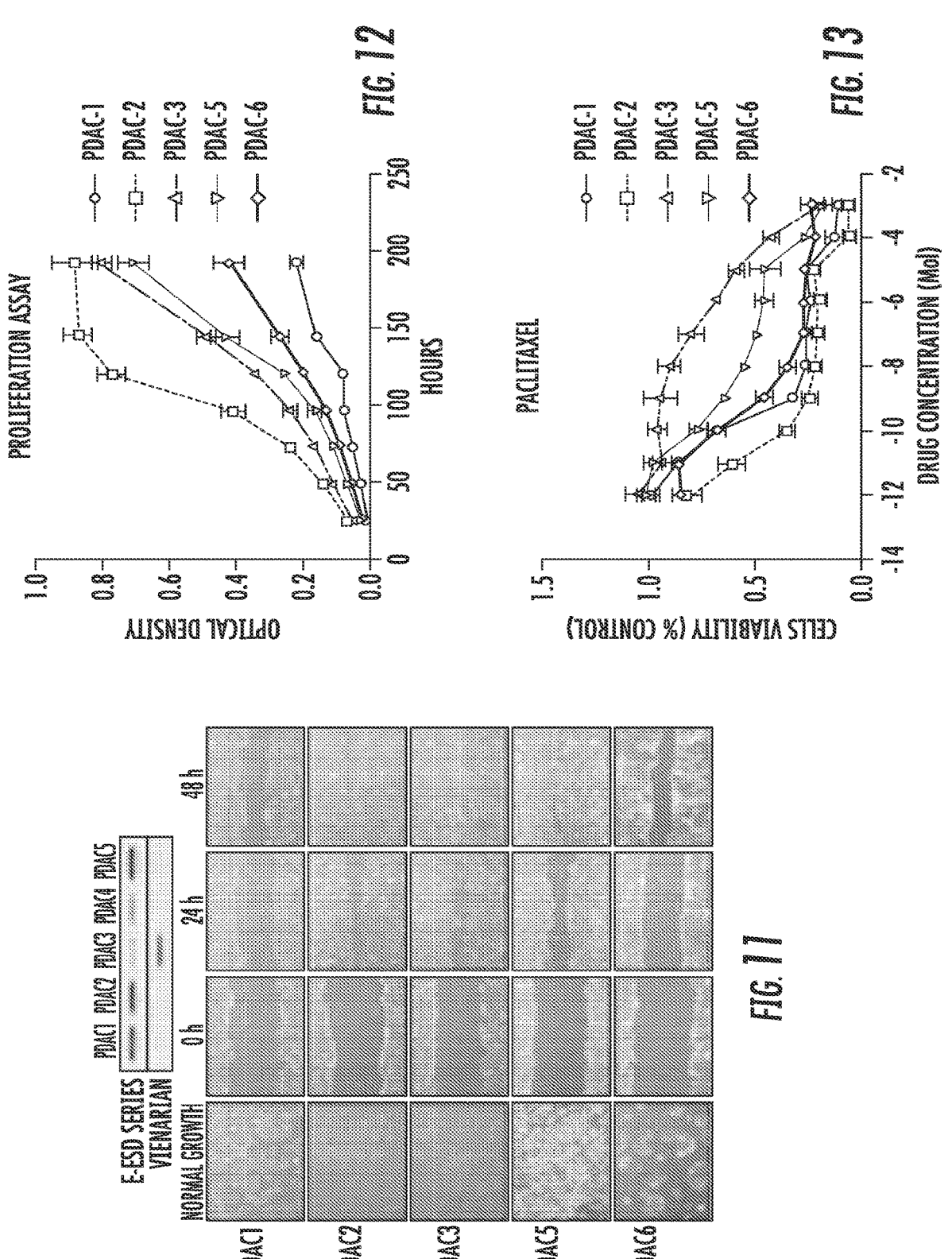
FIG. 11 is a set of micrographs showing five of the six pancreatic adenocarcinoma cell lines (PDAC 1-6) used in in vivo studies.
FIG. 12 is a graph showing the optical density over time of five of the six pancreatic adenocarcinoma cell lines (PDAC 1-6) used in in vivo studies.
FIG. 13 is a graph showing the cell viability at various drug concentrations of five of the six pancreatic adenocarcinoma cell lines (PDAC 1-6) used in in vivo studies.

As shown in FIGS. 11-13, six newly established pancreatic adenocarcinoma cell lines (PDAC 1-6) were generated from metastatic ascites in patients enrolled in an IRB approved protocol at Massachusetts General Hospital (five of the six PDAC lines are shown). The cell lines were orthotopically injected in NOD/SCID/γc immunodeficient mice to identify the optimal xenograft tumor model system for testing the drug eluting polymer device.

The orthotopic pancreatic xenografts formed tumors in mice with varying histologies. For example, cell line PDAC-6 developed the most desmoplastic response compared to other cell lines in vivo. Specifically, a Hematoxylin and Eosin stained PDAC-6 orthotopic xenograft showed epithelial tumor cells surround by desmoplastic stromal response. PDAC-3 was mesenchymal in appearance, migratory, and chemorsistant, while PDAC-6 was epithelial in appearance, has a high level of stroma, shows no migration, and is chemosensitive. Thus, the patient-derived cell lines reflect the variability of PDAC patients' response to chemotherapy, showing different in vitro and in vivo paclitaxel sensitivity.

Figure 7:
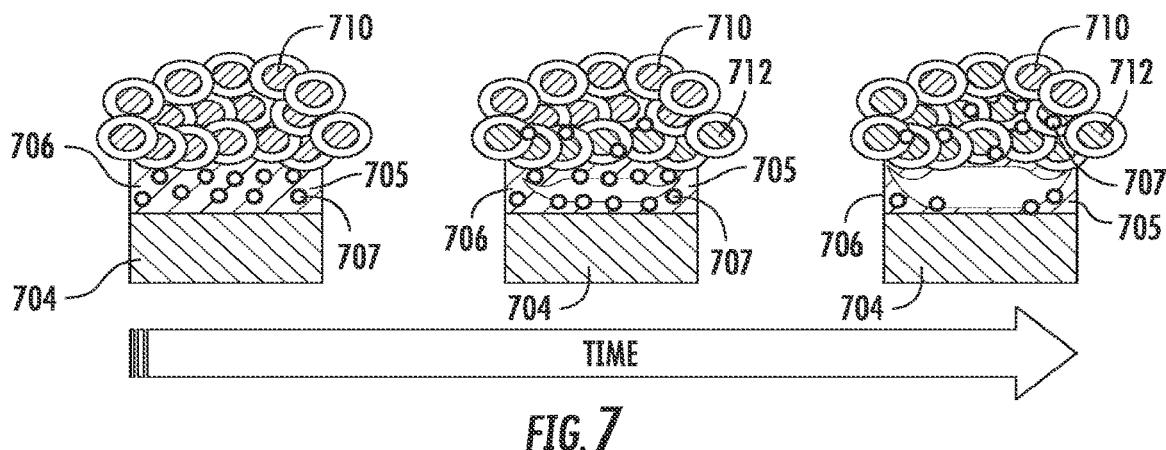
FIG. 7 is a diagram illustrating the treatment of tumor cells over time with a drug-eluting device.

A paclitaxel eluting device (PED) was implanted into the mice at week 4. The results of the mouse xenograft studies are shown in FIGS. 14-18. Overall, a decrease in relative tumor growth was observed in both the PDAC-3 and PDAC-6 cell lines with the use of a drug eluting device. That is, the mice tumors model data shows efficacy of the local drug delivery platforms for treating pancreatic cancer. FIG. 7 shows the PDAC cell reduction mechanism of the polymer-drug film 706. Specifically, upon implantation at a tissue site, the film 706, which is disposed on substratum 704 and includes a chemotherapeutic drug 707 and a degradable polymer 705, the polymer 705 degrades, triggering release of the drug 707 to the site. This hinders growth of the PDAC cells 710 at the tissue site, resulting in dead tumor cells 712.

Figures 14, 15, 16, 17:
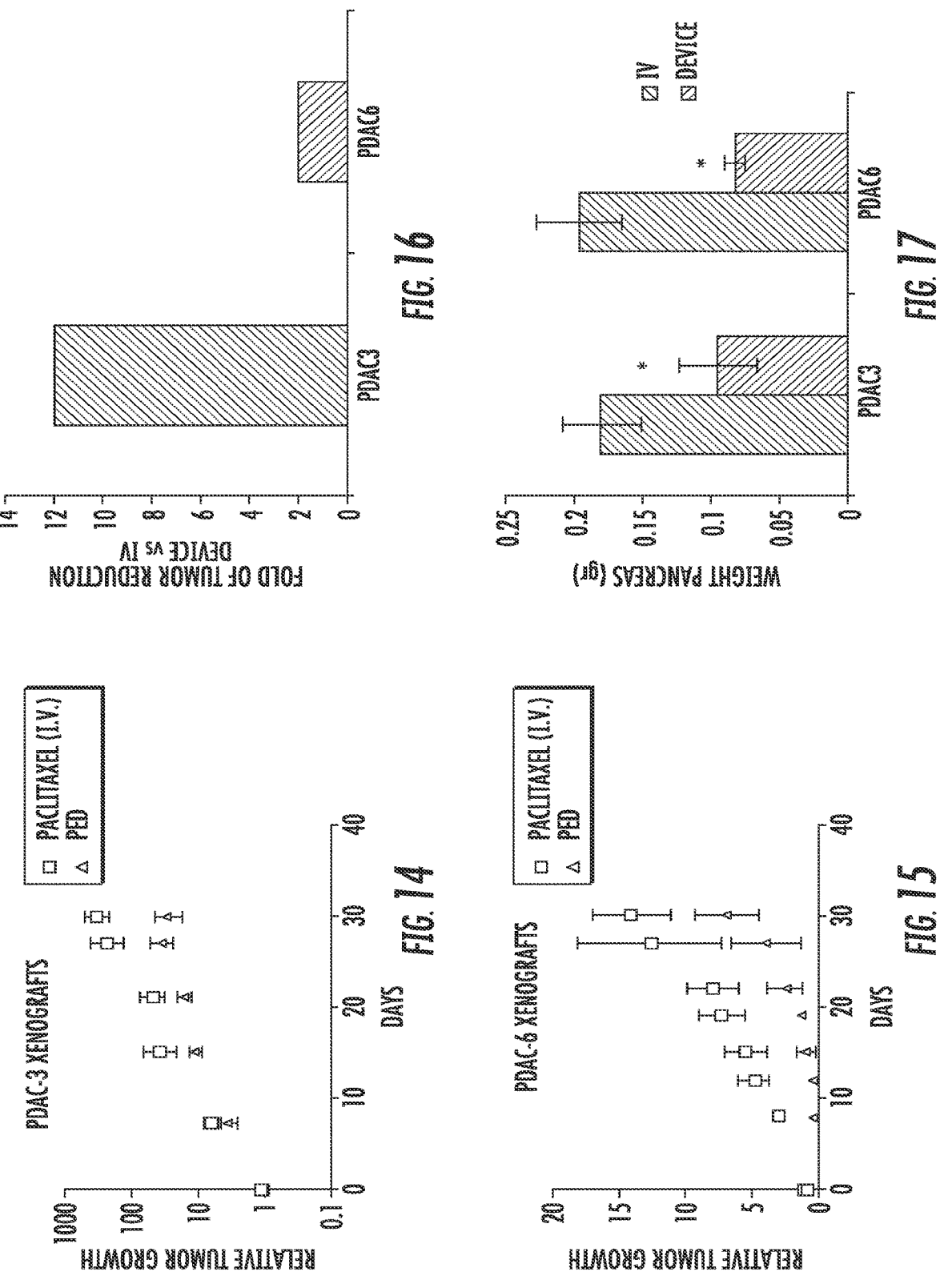
FIG. 14 is a graph showing the relative tumor growth over time of PDAC-3 when treated with a paclitaxel-eluting device versus when treated with paclitaxel intravenously.
FIG. 15 is a graph showing the relative tumor growth over time of PDAC-6 when treated with a paclitaxel-eluting device versus when treated with paclitaxel intravenously.
FIG. 16 is a graph showing the relative tumor reduction of a drug-eluting device versus intravenous drug treatment for PDAC-3 and PDAC-6.
FIG. 17 is a graph showing the weight of a pancreas treated with a drug-eluting device versus intravenous drug treatment for PDAC-3 and PDAC-6.

In FIGS. 14-18, the relative efficacy of the drug-eluting device (PED_20_400) was compared to intravenous (IV) systemic delivery, utilizing fluorescently-labeled paclitaxel to measure its distribution inside pancreatic xenografts. Higher intratumoral paclitaxel presence and a greater tumor growth inhibition were observed in mice having the implanted PED compared to mice treated with systemic administration of paclitaxel. Although neither of the cell lines was exposed to paclitaxel before, the PDAC-6 xenografts displayed an early tumor response while the PDAC-3 tumors needed roughly two weeks to show a clear tumor growth inhibition, recapitulating the in vitro paclitaxel sensitivity profiles. As shown in FIG. 16, the paclitaxel-eluting devices showing a 2 to 12 fold increase in tumor reduction as compared to systemic IV therapy.

Figure 18:
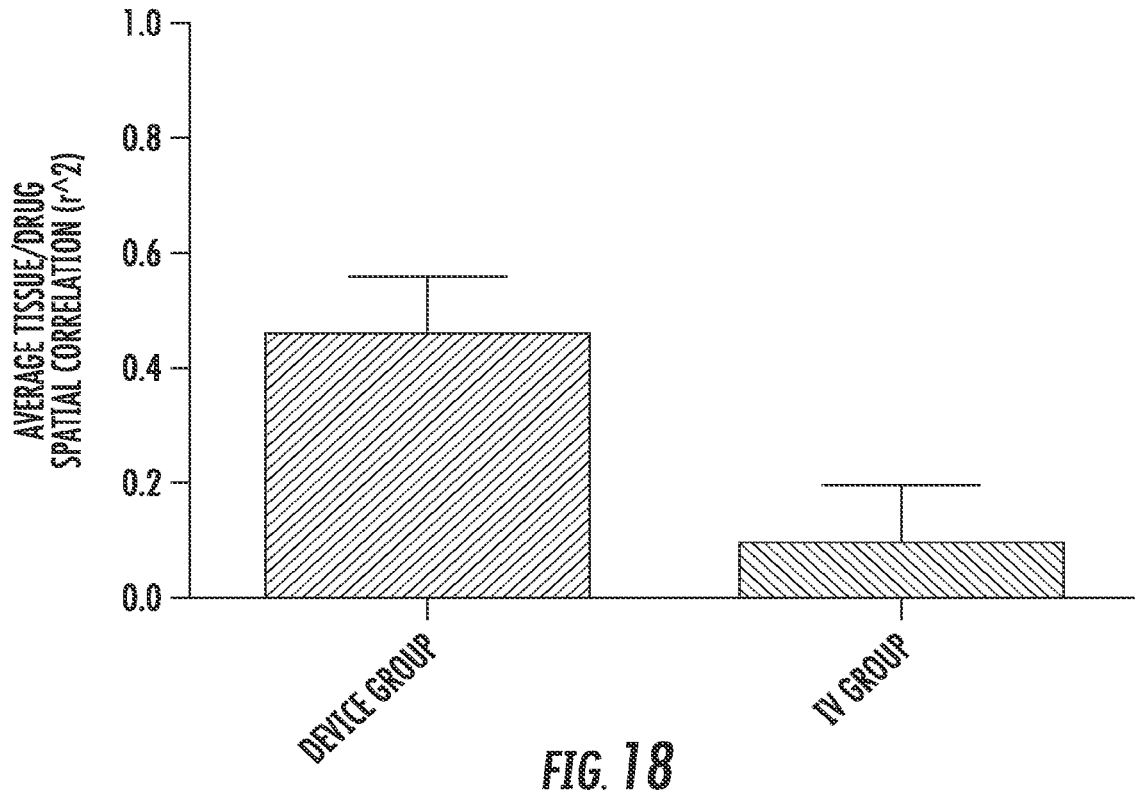
FIG. 18 is a graph showing the average tissue/drug spatial correlation of pancreatic sites treated with a drug-eluting device versus intravenous drug treatment.

Extracted tumor masses from PED-bearing mice macroscopically showed presence of fluorescent dye when observed under a dissecting microscope. To quantify intratumoral drug distribution, serial sections of the tumor perpendicular to the PED were imaged by quantitative confocal microscopy. Paclitaxel tissue retention was markedly higher in tumors treated with the PED compared to intravenous dosing. Tissue penetration within the tumor was quantified by line scans starting from the entry site for paclitaxel (PED—tumor/device interface; IV—vessels). Remarkably, paclitaxel penetration depth extended up to 400 microns for the PED, while IV administration was limited to presence only in a 10 micron radius around the vessels. Moreover, as shown in FIG. 18, by mapping the images with a matlab algorithm, we evaluated that targeted release allowed for increased paclitaxel/tumor co-localization with a percentage area almost 5 fold higher than in the case of systemic IV delivery. That is, the paclitaxel-eluting devices resulted in 5 times the drug presence and distribution within the tumor as compared to IV therapy.

In summary, a degradable polymer film was developed to provide a highly tunable sustained release of drug in a device suitable for implantation in a pancreatic orthotopic xenograft mouse model. This device was well tolerated in all mice and surprisingly demonstrated significant tumor response in two different human PDAC cell line xenografts compared to equivalent systemic dosing. Moreover, significantly higher tissue penetration of drug was observed using the PED as compared to systemic intravenous dosing. This higher delivery was achievable without any adverse effects to the mice and with notable reduction of viable tumor mass for the pancreatic cell line xenografts.

These results highlight the potential of these devices to deliver high doses of cytotoxic agents as well as novel therapeutics providing a new modality to treat tumors by bypassing inherent drug delivery barriers. Specifically, these results show that effective local delivery of conventional chemotherapeutic agents can overcome intrinsic PDAC chemoresistance, opening new therapeutic strategies to improve the outcomes of such patients. Utilizing a degradable polymer, a multi-purpose drug-eluting device can be designed as described herein to locally deliver high payloads of cytotoxic agents and reach higher intratumoral concentrations not achievable with systemic administration due to dose-limiting toxicity. Moreover, releasing sustained local concentrations of chemoactive agents may increase the longevity of the device and inhibit local tumor progression. This would significantly improve the ability to palliate biliary obstruction symptoms, reduce the number of re-stenting procedures, and improve the quality of life in patients.

Furthermore, because PDAC patients may respond very differently to chemotherapy, it is advantageous that these devices can be personalized to release different amounts of drugs at a desired release kinetic profile, to maximize the cytotoxic effects of current or future anti-neoplastic agents and minimize systemic toxicity to achieve a greater tumor response and patient survival.

Modifications and variations of the methods and devices described herein will be obvious to those skilled in the art from the foregoing detailed description. Such modifications and variations are intended to come within the scope of the appended claims.

We claim:

1. An implantable device for delivering a drug to a tumor of a patient, comprising:
   a first film layer comprising a first polymer, the first film layer being free from the drug; and
   a second film layer adhered to the first film layer, the second film layer comprising the drug and a second polymer;
   wherein the second polymer comprises poly (lactic-co-glycolic acid) and is configured to degrade within 30 and 120 days after implantation of the implantable device directly onto the tumor;
   wherein a therapeutically effective amount of the drug is released from the second film layer following a first period of from 2 days to 14 days after the implantation of the implantable device onto the tumor, wherein a sub-therapeutically effective amount of the drug or no drug is released during the first period;
   wherein the release of the drug from the second film layer is controlled solely by the in vivo degradation of the second polymer; and
   wherein the first and second film layers form a flexible, self-supporting structure.

2. The implantable device of claim 1, wherein the release of the drug from the second film layer, following the first period, has a release rate that is substantially linear for at least three days.

3. The implantable device of claim 1, wherein the drug is paclitaxel.

4. The implantable device of claim 3, wherein the second film layer comprises 50:50 poly (lactic-co-glycolic acid).

5. The implantable device of claim 3, wherein the first film layer comprises poly (lactic-co-glycolic acid).

6. The implantable device of claim 5, wherein the first film layer comprises 75:25 poly (lactic-co-glycolic acid).

7. The implantable device of claim 1, wherein the first period is from 2 days to 4 days.

8. The implantable device of claim 1, wherein after the first period, the therapeutically effective amount of the drug is released from the second film layer at a rate of at least about 1 mg/day.

9. The implantable device of claim 1, wherein after the first period, the therapeutically effective amount of the drug is released at a mean average amount of 5-125 mg/day.

10. The implantable device of claim 1, wherein the in vivo degradation of the second polymer is hydrolytic degradation.

11. The implantable device of claim 3, wherein the second film layer comprises 1-10 wt % paclitaxel.

12. An implantable device for delivering paclitaxel to a tumor of a patient, comprising:
    a first film layer comprising a first polymer, the first film layer being free from paclitaxel; and
    a second film layer adhered to the first film layer, the second film layer comprising paclitaxel and a second polymer;
    wherein the second polymer comprises poly (lactic-co-glycolic acid) and is configured to degrade within 30 and 120 days after implantation of the implantable device directly onto the tumor;
    wherein a therapeutically effective amount of the paclitaxel is released from the second film layer following a first period of from 2 days to 14 days after the implantation of the implantable device onto the tumor, wherein a sub-therapeutically effective amount of the paclitaxel or no paclitaxel is released during the first period;

wherein the release of the paclitaxel from the second film layer is controlled solely by the in vivo degradation of the second polymer; and wherein the first and second film layers form a flexible, self-supporting structure.

13. The implantable device of claim 12, wherein the release of the paclitaxel from the second film layer, following the first period, has a release rate that is substantially linear for at least three days.

14. The implantable device of claim 12, wherein the second film layer comprises 50:50 poly (lactic-co-glycolic acid).

15. The implantable device of claim 14, wherein the first film layer comprises poly (lactic-co-glycolic acid).

16. The implantable device of claim 14, wherein the first film layer comprises 75:25 poly (lactic-co-glycolic acid).

17. The implantable device of claim 12, wherein the first period is from 2 days to 4 days.

18. The implantable device of claim 12, wherein after the first period, the therapeutically effective amount of the paclitaxel is released from the second film layer at a rate of at least about 1 mg/day.

19. The implantable device of claim 12, wherein after the first period, the therapeutically effective amount of the paclitaxel is released at a mean average amount of 5-125 mg/day.

20. The implantable device of claim 12, wherein the second film layer comprises 1-10 wt % paclitaxel.

21. The implantable device of claim 12, wherein the second film has a thickness from about 5 μm to about 1000 μm.

22. The implantable device of claim 12, wherein the second film has a thickness from about 5 μm to about 500 μm.

23. The implantable device of claim 12, wherein the second film is obtained by solvent evaporation of a solution having a concentration of the PLGA from about 5 to about 40 percent weight by volume.

24. The implantable device of claim 12, wherein the second film is obtained by solvent evaporation of a solution having a concentration of the PLGA from 5 to 20 percent weight by volume.

25. The implantable device of claim 12, wherein (i) the PLGA is PLGA 50:50; (ii) the second film is obtained by solvent evaporation of a solution having a concentration of the PLGA from 5 to 20 percent weight by volume; (iii) the film comprises from about 1 wt % to about 10 wt % paclitaxel; or (iv) any combination of (i)-(iii).

\* \* \* \* \*